United States Patent [19]
Reams, III et al.

[11] Patent Number: 5,902,109
[45] Date of Patent: May 11, 1999

[54] REDUCED FRICTION SCREW-TYPE DENTAL IMPLANT

[75] Inventors: James W. Reams, III, Stuart; Ralph E. Goodman, West Palm Beach; Dan Paul Rogers, Royal Palm Beach, all of Fla.

[73] Assignee: Implant Innovations, Inc., Palm Beach Gardens, Fla.

[21] Appl. No.: 08/782,056

[22] Filed: Jan. 13, 1997

Related U.S. Application Data

[60] Provisional application No. 60/010,179, Jan. 18, 1996, and provisional application No. 60/011,034, Feb. 2, 1996.

[51] Int. Cl.$^6$ ........................................................ A61C 8/00
[52] U.S. Cl. ................................................................ 433/174
[58] Field of Search ...................................... 433/172, 173, 433/174, 201.1

[56] References Cited

U.S. PATENT DOCUMENTS

| | | | |
|---|---|---|---|
| 1,401,862 | 8/1921 | Linkow et al. ................................. | 13/30 |
| 3,877,339 | 4/1975 | Muenchinger ................................. | 85/9 |
| 3,937,120 | 2/1976 | Munse ........................................... | 85/47 |
| 3,971,135 | 7/1976 | Leu ............................................... | 32/48 |
| 4,104,446 | 8/1978 | Johnson ...................................... | 428/585 |
| 4,293,302 | 10/1981 | Hassler et al. ............................. | 433/173 |
| 4,414,966 | 11/1983 | Stednitz ...................................... | 252/359 |
| 4,463,753 | 8/1984 | Gustilo ........................................ | 128/92 |
| 4,468,200 | 8/1984 | Munch ....................................... | 433/174 |
| 4,484,570 | 11/1984 | Sutter et al. ................................ | 128/92 |
| 4,490,116 | 12/1984 | Deutsch et al. ............................ | 433/215 |
| 4,547,157 | 10/1985 | Driskell ...................................... | 433/173 |
| 4,583,898 | 4/1986 | Sygnator ..................................... | 473/524 |
| 4,668,191 | 5/1987 | Plischka ..................................... | 433/174 |
| 4,722,688 | 2/1988 | Lonca ......................................... | 433/173 |
| 4,787,792 | 11/1988 | Jesson et al. ............................... | 411/387 |
| 4,826,434 | 5/1989 | Krueger ...................................... | 433/174 |
| 4,863,383 | 9/1989 | Grafelmann ................................ | 433/174 |
| 4,915,628 | 4/1990 | Linkow et al. ............................. | 433/173 |
| 4,978,350 | 12/1990 | Wagenknecht .............................. | 606/72 |
| 5,000,639 | 3/1991 | Hinkley et al. ............................. | 411/418 |
| 5,000,686 | 3/1991 | Lazzara et al. . | |
| 5,026,285 | 6/1991 | Dürr et al. .................................. | 433/173 |
| 5,061,181 | 10/1991 | Niznick ...................................... | 433/174 |
| 5,064,425 | 11/1991 | Branemark et al. ........................ | 600/72 |
| 5,076,788 | 12/1991 | Niznick ...................................... | 433/173 |
| 5,269,685 | 12/1993 | Jörnéus et al. ............................. | 433/174 |
| 5,312,256 | 5/1994 | Scortecci ................................... | 433/174 |
| 5,324,199 | 6/1994 | Branemark ................................ | 433/174 |
| 5,395,195 | 3/1995 | Fulmer ...................................... | 411/386 |
| 5,435,723 | 7/1995 | O'Brien .................................... | 433/174 |
| 5,533,898 | 7/1996 | Mena ........................................ | 433/173 |
| 5,549,677 | 8/1996 | Durr et al. .............................. | 433/174 X |
| 5,702,443 | 12/1997 | Branemark ................................ | 623/11 |

FOREIGN PATENT DOCUMENTS

| | | | |
|---|---|---|---|
| 0 424 734 | 5/1991 | European Pat. Off. .......... | A61C 8/00 |
| 0 530 160 | 3/1993 | European Pat. Off. .......... | A61C 8/00 |

OTHER PUBLICATIONS

Stryker Dental Implants, Price List Effective Jun. 1, 1993 (46 pages).
Stryker Dental Implants, brochure (undated) (5 pages).
Richards Technical Publication, Bone Screw Technical Information, 1980 (15 pages).

*Primary Examiner*—Nicholas D. Lucchesi
*Attorney, Agent, or Firm*—Arnold, White & Durkee

[57] ABSTRACT

An implant for implantation into bone tissue having an exterior surface includes an elongated body and at least one thread. The elongated body has a distal end portion for being submerged in the bone tissue, a proximal end portion for being located near the exterior surface of the bone tissue, a central axis, and an outer surface. When viewed in cross-section, the elongated body has a non-circular cross-section. The non-circular cross-section includes a plurality of lobes and a plurality of dwells. Each of the plurality of dwells is disposed between adjacent ones of the plurality of lobes. The thread extends radially outward with respect to the central axis from the outer surface of the elongated body between the distal end portion and the proximal end portion. As the implant is screwed into the bone tissue, only the lobes on the elongated body engage the bone tissue. Because no contact exists between the dwells and the bone tissue, the amount of torque required to insert the implant is reduced.

45 Claims, 8 Drawing Sheets

REDUCED FRICTION SCREW-TYPE DENTAL IMPLANT

CROSS REFERENCES RELATED APPLICATIONS

This is a complete application claiming the benefit of now abandoned Provisional Patent Applications Serial No. 60/010,179; Filed Jan. 18, 1996 and Serial No. 60/011,034; Filed Feb. 2, 1996

FIELD OF THE INVENTION

This invention relates to improvements in screw-type dental implants and, in particular, to reducing the friction between the main body of such an implant and the side walls of a bore provided in living jawbone when the implant is screwed into that bore.

BACKGROUND OF THE INVENTION

Screw-type dental implants are widely used and have been known for a number of years. They are made in two general types. The first type is a self-tapping implant, in that it can be threaded into a pre-drilled bore in a jawbone without pre-tapping the bore. The second type is a non-self-tapping implant that requires pre-tapping of the bore. In either type, the implant has a generally cylindrical main body which bears one or more external screw threads on its outer surface. These external thread(s) engage corresponding internal thread(s) cut into the wall of the bore to provide initial stabilization of the implant in the bore.

A problem commonly encountered is the friction between the implant and the bone walls defining the bore. The friction is proportional to the penetration depth of the implant into the bone, the diameter of the bore, and the hardness of the bone at the site of the bore. The torque that must be applied to insert the implant into the bore is proportional to the friction. High torque puts strains on the implant, on the tools used to place the implant in the bore, and on the bone. Furthermore, in cases where high torque is required to insert the implant, there is a greater risk of damage to the implant, the tools, and the bone. Consequently, there is a continuing need to design a screw-type dental implant which minimizes the torque needed to install it into living jawbone.

SUMMARY OF THE INVENTION

In the design of screw-type dental implants as presently practiced, the main body of the implant is generally cylindrical. The thread peaks and thread roots (troughs) are each on the locus of a cylinder with each cylinder being concentric about the cylinder axis of the main body.

It is a primary object of this invention to provide an improved dental implant that reduces the torque required to install the implant into the bore in the jawbone and fix it in place in that bore.

Another object of the invention is to provide an improved screw-type dental implant that reduces the torque required to install the implant by reducing the friction between the implant and the sidewalls of the bore. A related object is to reduce the time and effort required to install the implant.

An additional object of the invention is to provide an improved screw-type dental implant that will resist forces tending to unscrew it from the bore after it has been installed.

Other objects and advantages of the invention will become apparent from the following description and the accompanying drawings.

In accordance with the present invention the foregoing objectives are realized by providing an improved screw-type dental implant comprising a generally cylindrical body having a threaded outer surface for securing the implant to the walls of a preformed hole in a jawbone. At least one dimensional characteristic of the body is varied with respect to its azimuthal position around the cylinder axis so as reduce the overall frictional contact between the implant body and the walls of the bore during installation of the implant. The variance in this dimensional characteristic also serves to resist turning of the body in the bore after the bone in the side walls of the bore has grown onto the implant body in the normal healing process. Examples of such a dimensional characteristic include:

a) the radius of the locus of the peaks of the threads;
b) the radius of the locus of the troughs of the threads;
c) thickness of the threads; and
d) angle between the faces of the threads.

An embodiment of the invention may employ these and other characteristics variably according to the invention, singly or in combination with one or more of the others. The variation employed can be cyclical or random around the cylinder axis. It can be synchronous or it can progress or regress with respect to the axis as its proceeds along the axis from one end of the body toward the other end.

Generally, the invention may provide an implant in which some portions of (for example) the peaks or troughs of the threads are on the original cylinder lacking the varied radius while other portions of the same characteristic are within that cylinder so that they make less or no contact with the walls of the hole. This design has two effects. First, by reducing the area of implant body that makes contact with the walls of the bore, the friction between the implant and the bone during installation of the implant is reduced. And second, after the bone has grown during healing to touch the implant body around the irregular (non-circular) portions thereof, the implant body resists turning in the bone more than would a typical implant having a cylindrical body lacking the radial-dimension variations of the invention.

Similar considerations apply to varying the thickness of the threads with respect to azimuthal position around the cylinder axis. One technique for varying the radius of the locus of the thread peaks is also effective to vary the thickness of the threads synchronously with variation in the radius, so that these two characteristics can be employed simultaneously with one manufacturing process step.

In an exemplary embodiment of the invention that is described in this specification, the main body is modified to a non-circular cross-sectional shape having four lobes equally spaced around the cylinder axis. The lobes are aligned parallel to the cylinder axis, and the implant has a tapered end section with four self-tapping cutting edges spaced equally around the cylinder axis substantially in line with the lobes. This embodiment is described in the accompanying drawings, in which:

DETAILED DESCRIPTION OF THE DRAWINGS

Figure 1:
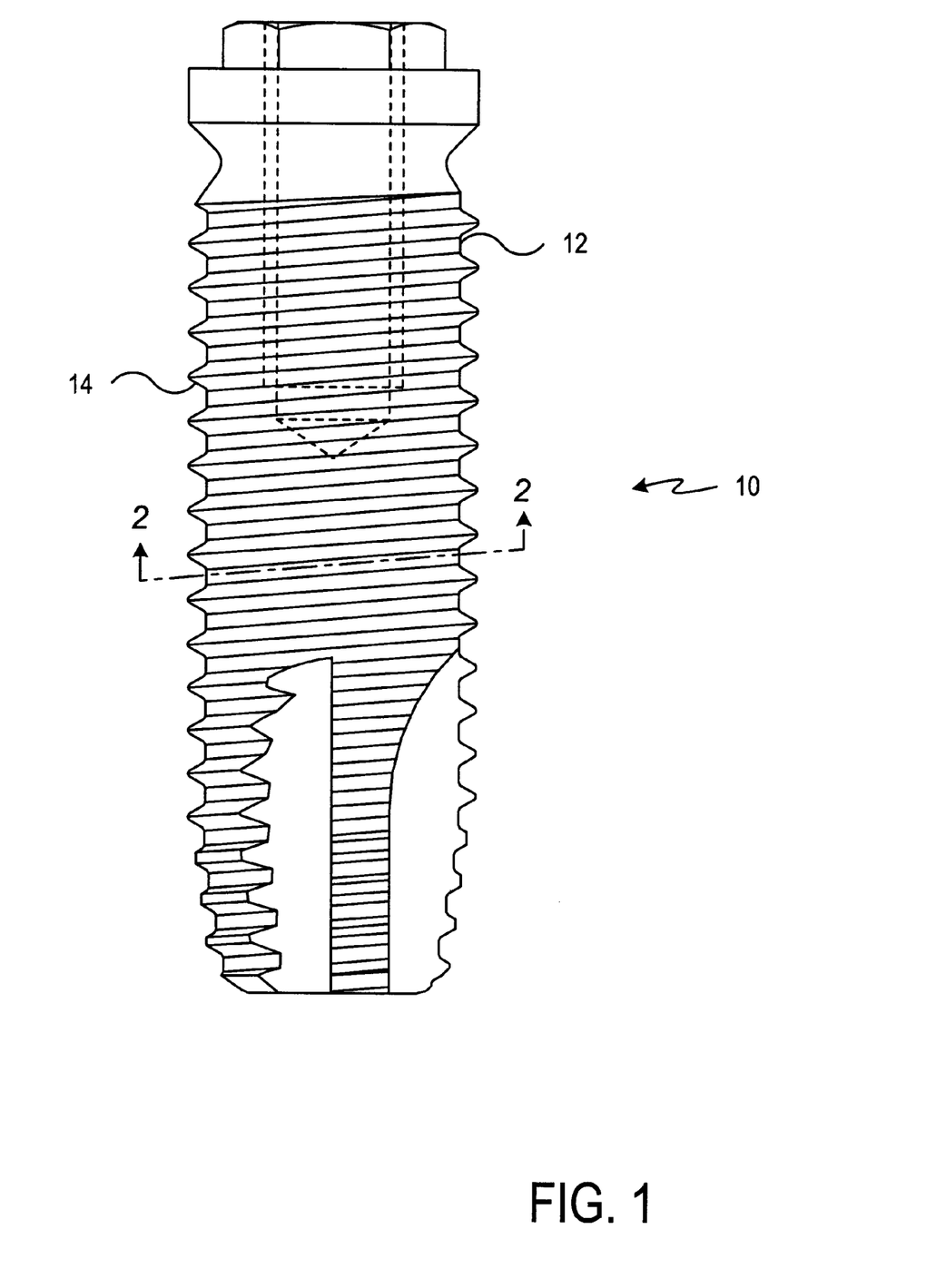
FIG. 1 is an implant incorporating the present invention.

FIG. 1 illustrates an implant 10 which incorporates the present design. The implant 10 has a main body 12 with external threads 14. A sectional line 2—2 is a helical section line in that it is taken along the trough between two adjacent threads 14. This section is shown in FIG. 2.

Figures 2, 3, 4, 5, 6:
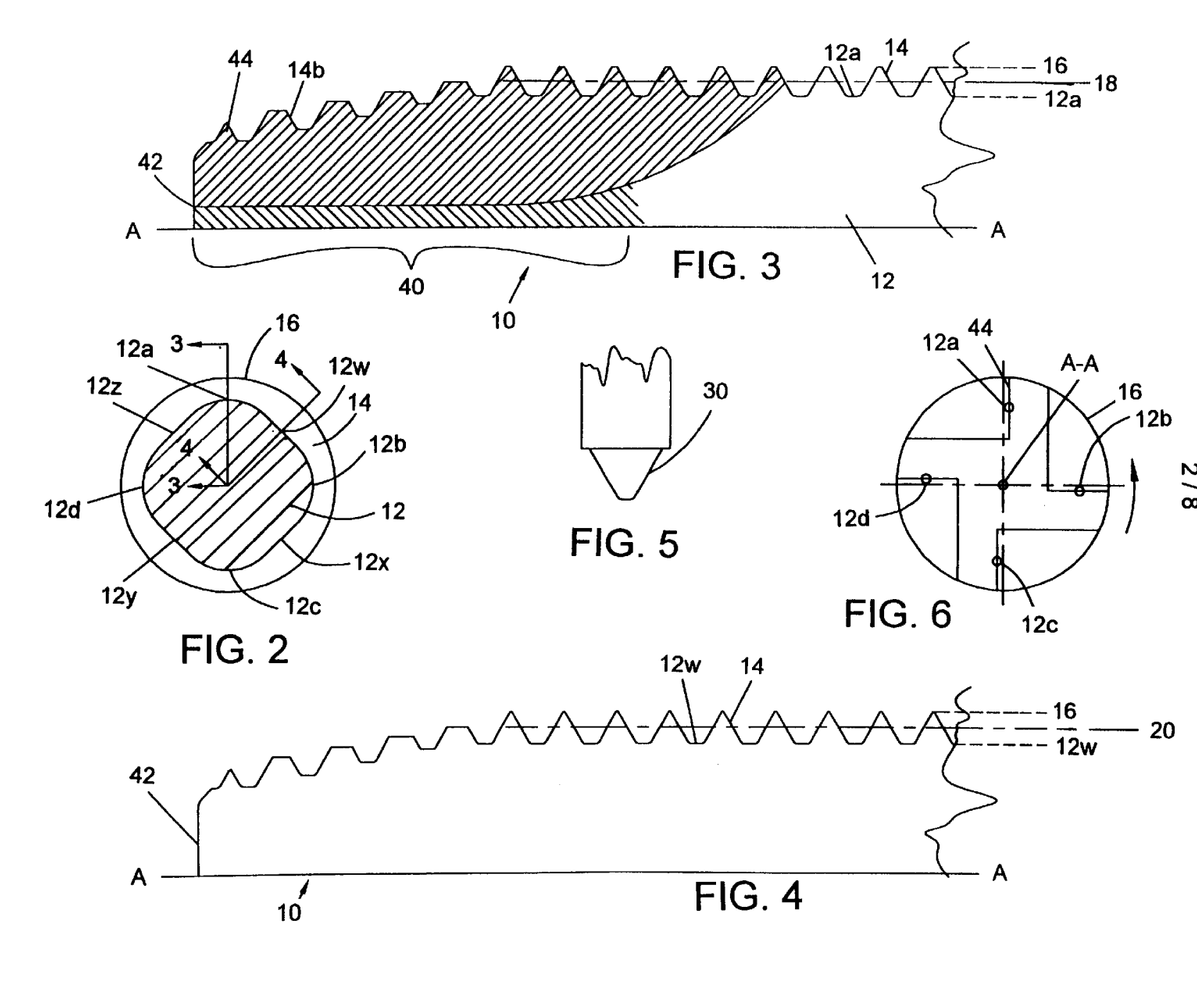
FIG. 2 is a helical section taken along line 2—2 in FIG. 1.
FIG. 3 is a longitudinal half-section taken on line 3—3 in FIG. 2.
FIG. 4 is a longitudinal half-section taken on line 4—4 in FIG. 2.
FIG. 5 represents a thread-forming tool useful to make the implant.
FIG. 6 schematically illustrates a property of the invention.

In FIG. 2, the main body 12 of the implant 10 has a non-circular shape as seen transverse to the longitudinal axis A—A (FIG. 2), with external threads 14 having peak diameters in a cylindrical locus 16. The non-circular shape has four lobes 12a, 12b, 12c and 12d arrayed symmetrically around the axis A—A. The non-circular shape can be a variety of shapes including rhombic or rhomboidal. One of these lobes, 12a, defines the troughs of the threads 14 which are on the main body 12, shown in FIG. 3. Between the lobes are four equally-spaced dwell regions 12w, 12x, 12y and 12z, of the main body 12. The mid-point of one of these dwell regions, falling on line 4—4 in FIG. 2, defines the troughs of the threads 14 as shown in FIG. 4. The troughs defined by dwell 12w in FIG. 4 are deeper than the troughs defined by lobe 12a in FIG. 3. The peak diameters of the threads 14 on the main body 12 are the same in both FIGS. 3 and 4. The threads 14 are cut deeper in the dwell region 12w illustrated in FIG. 4 than they are cut in the lobe region 12a illustrated in FIG. 3, without the peak diameter changing in either location.

The threads 14 may be cut with a tool such as the tool 30 shown in FIG. 5, which has a shape that can be pushed into the main body 12 as it is turned in a lathe according to a cyclical pattern to form the alternating lobes and dwell regions. When this tool 30 is pushed into the main body 12 far enough to form a dwell region, the threads 14 are made thinner in the region of the larger pitch diameter 18 as compared with the thread shape formed when the tool is pushed into a shallower depth to form a lobe. As a result, the pitch diameter 18 of the threads 14 shown in FIG. 3 is larger than the pitch diameter 20 of the deeper threads shown in FIG. 4.

The illustrated dental implant 10 has a tapered end part 40 wherein both the peaks and the troughs of the threads 14b taper on respective substantially conical loci toward the extreme end 42 of the main body 12. This tapered end part 40 is fitted with four self-tapping cutting means arrayed symmetrically around the axis A—A, of which only 144 is shown in FIG. 3. As is apparent in FIG. 3, each cutting means is aligned with one of the lobes 12a–d, respectively, and therefore with the larger pitch diameter. This relationship is schematically illustrated in FIG. 6.

Figure 7:
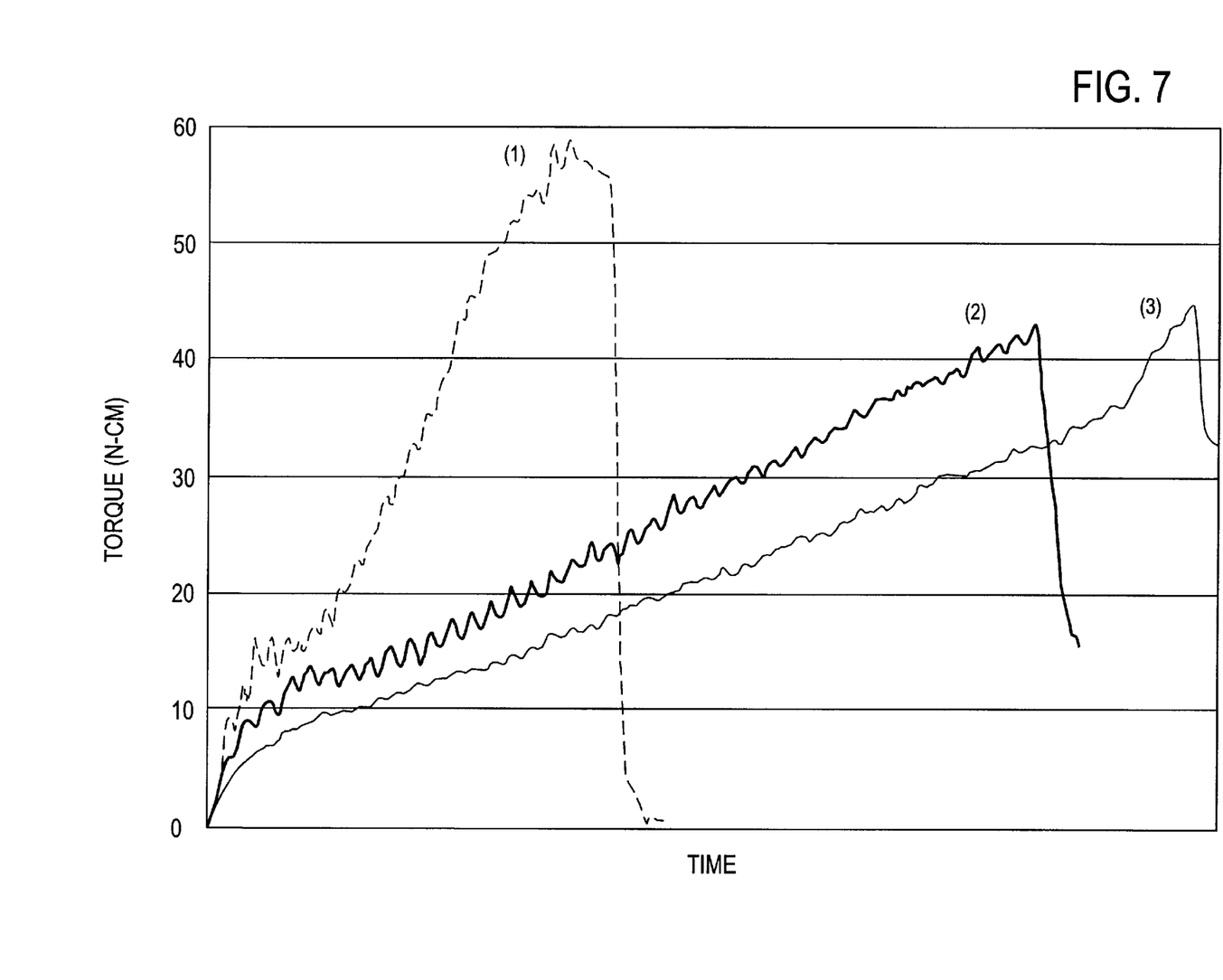
FIG. 7 is a graph illustrating the reduced torque accomplished due to the present invention.

FIG. 7 illustrates the benefits derived from the present invention in graphical form. The dashed line (1) shows the torque of a 6.0 mm diameter implant which does not incorporate the present invention as it is screwed into a test fixture. The torque reaches nearly 60 N×cm. The darker solid line (2) is a 6.0 mm diameter implant utilizing the present invention shown in FIGS. 1–6. The peak torque is approximately 40 N×cm, which is substantially less than dashed line (1). The thin solid line (3) is the torque required for a smaller 3.75 mm diameter implant that does not incorporate the design of the present invention. As can be seen, the peak torque for the 6.0 mm implant incorporating the present invention is similar to the torque requirement for the much smaller 3.75 mm implant. Furthermore, the rate at which the torque of darker line (2) increases is gradual making installation easier.

A further note concerning FIG. 7 is that the maximum torque for the machine screwing the implants into the test fixture was set at approximately 60 N×cm. The 6.0 mm implant without the present invention, dashed line (1), could not be fully screwed into the test fixture with this limit on the torque. Consequently, the quick fall in dashed line (1) indicates the time at which the machine reached its torque limit. The fall in the darker solid line (2) indicates the point of full installation. Because the number of threads per inch on both 6.0 mm specimens was the same, the time at which both 6.0 mm specimens should have reached the desired full-installation point should have been the same since the revolutions per minute of the machine in each test were the same. Thus, because solid line (2) drops off about at twice the time as dashed line (1), the implant lacking the claimed invention was only capable of being inserted about half the desired installation depth into the test fixture.

Figure 8:
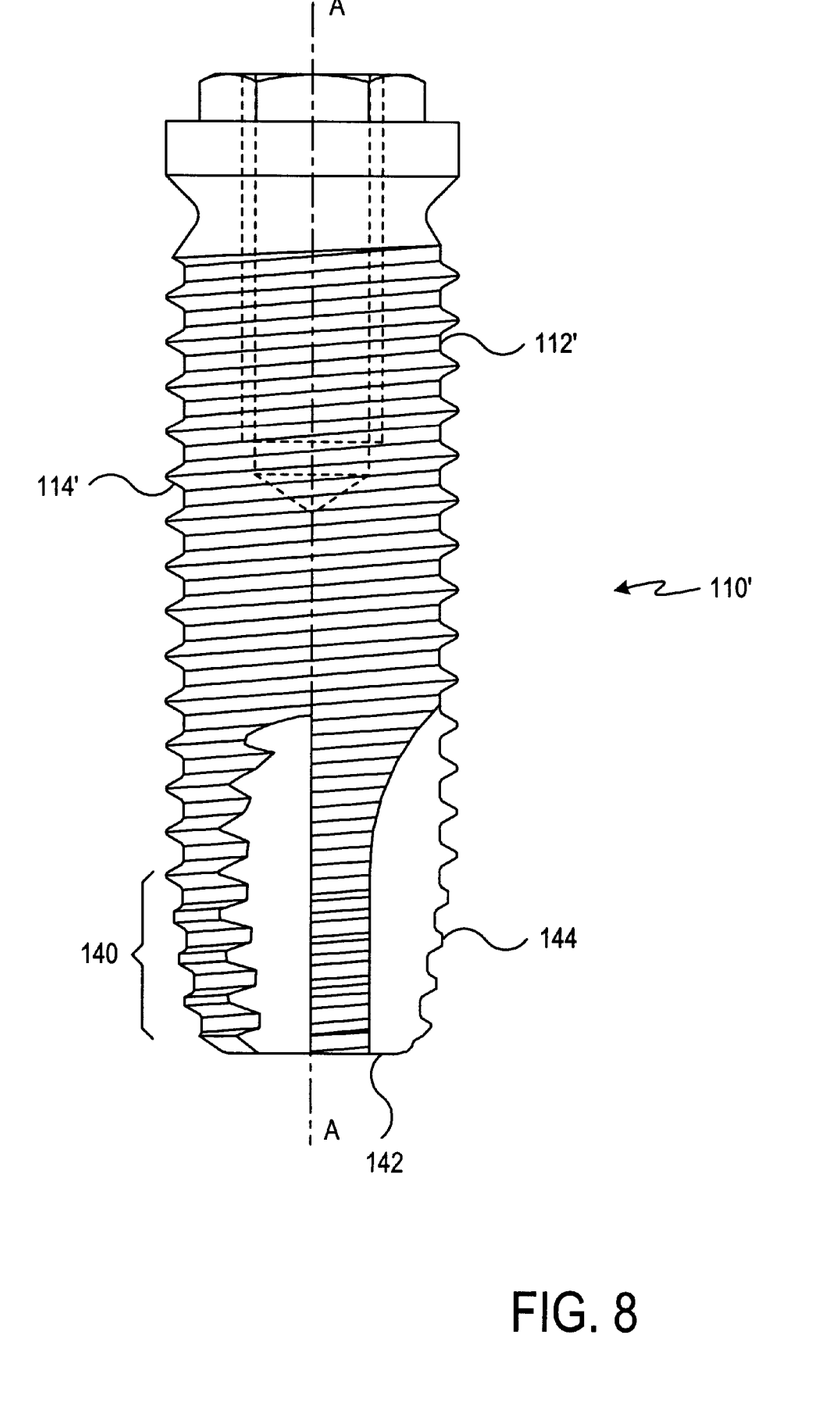
FIG. 8 is another implant which may incorporate an alternative embodiment of the present invention.
Figure 9:
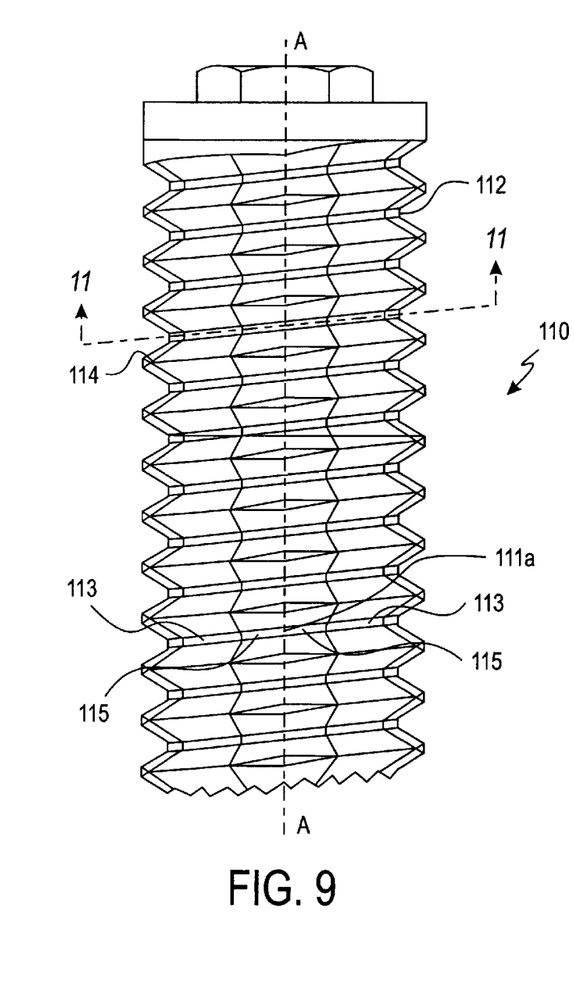
FIG. 9 is partial view of an implant incorporating the present invention.

FIG. 8 illustrates a typical implant 110' which may incorporate an alternative embodiment of the present design. The implant 110' has a main body 112' with external threads 114'. FIG. 9 illustrates the details of the alternative embodiment of the present invention on the threads 114 of the implant 110. The top portion of the implant 110' in FIG. 9 has a slightly different configuration than the top portion of the implant 110 in FIG. 8. As with the previous embodiment of FIGS. 1–7, the alternative embodiment of the present invention relates to the threads 114 and can be incorporated on any implant regardless of the configuration at its top. A sectional line 11—11 in FIG. 9 is a helical section line in that it is taken along the trough between two adjacent threads 114 as it spirals up the implant 110. This section is shown in FIG. 11.

Figure 11:
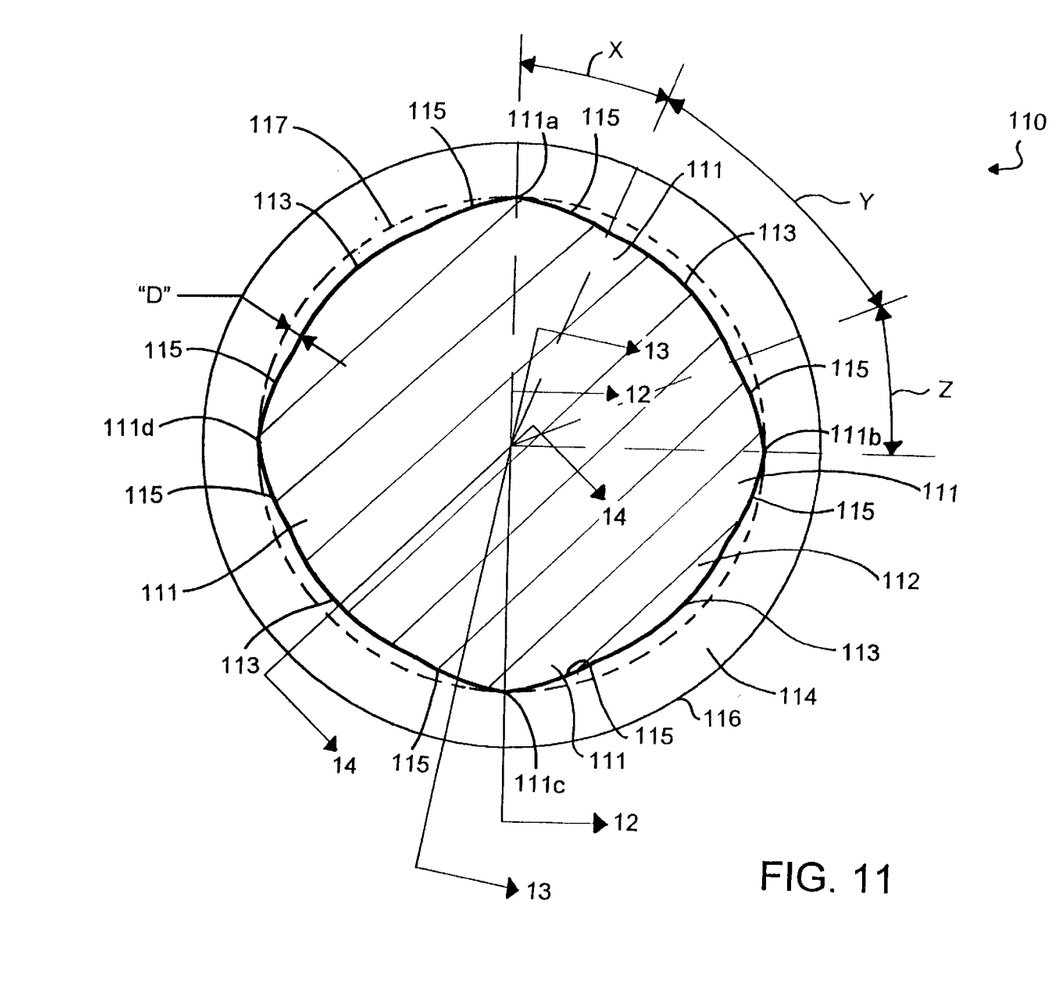
FIG. 11 is a helical section taken along line 11—11 in FIG. 8.

In FIGS. 9 and 11, the main body 112 of the implant 110 has a non-circular shape as seen transverse to the longitudinal axis A—A, with external threads 114 having major diameters in a cylindrical locus 116. Four lobes 111 are arrayed symmetrically around the axis A—A with peak minor diameters 111a, 111b, 111c, and 111d following along locus 117. Between the lobes 111 are four equally-spaced dwell regions 113 of the main body 112. A drop region 115 is located between each peak minor diameter 111a–111d and each adjacent dwell region 113. In the dwell region 113, the distance "D" represents the spacing between the body 112 of the implant 110 and the surface of the bone tissue.

Figure 10:
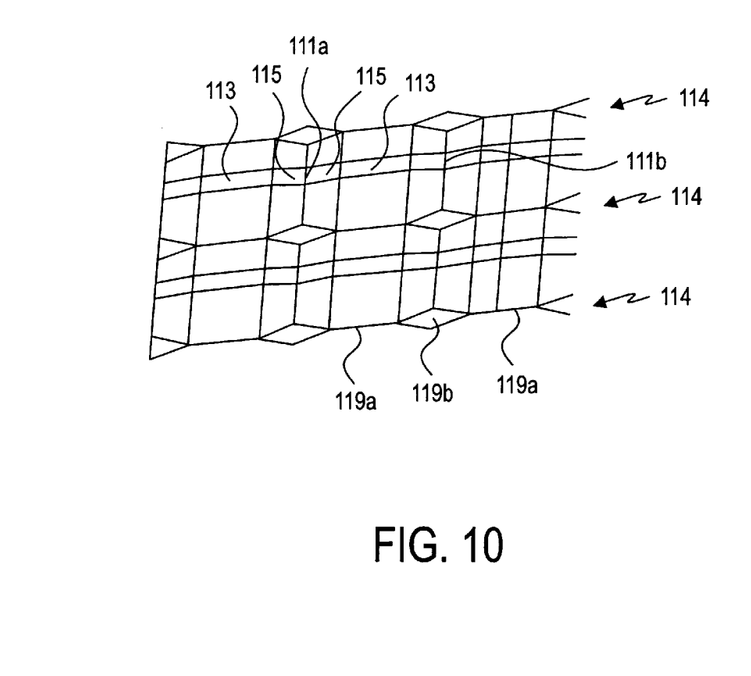
FIG. 10 illustrates three vertically-adjacent threads unrolled.

To assist in visualizing the present invention, FIG. 10 illustrates three vertically adjacent threads 114 unrolled from the implant 110 and the troughs therebetween. The peak minor diameter 111a is shown with the drop regions 115 on either side. The dwell regions 113 are shown adjacent the drop regions 115. The major diameter of the threads 114 lies on an edge at region 119a near the dwell regions 113. Near the drop regions 115 and the peak minor diameters of the lobes 111, the major diameter of the threads 114 lies on a surface 119b. The shape of surface 119a depends on the structure and depth of the drop regions 115 and the lobes 111.

Angles X and Z in FIG. 11 represent the angular position over which drop regions 115 occur and are generally less than angle Y. In one embodiment, angles X and Z are the same value. In a preferred embodiment, angles X and Z are approximately 22.5° while angle Y is approximately 45° such that the summation of angles X, Y, and Z is substantially 90°. If only three lobes were employed, then the summation of angles X, Y and Z would be substantially 120° if the lobes were symmetrically spaced.

Figure 12:
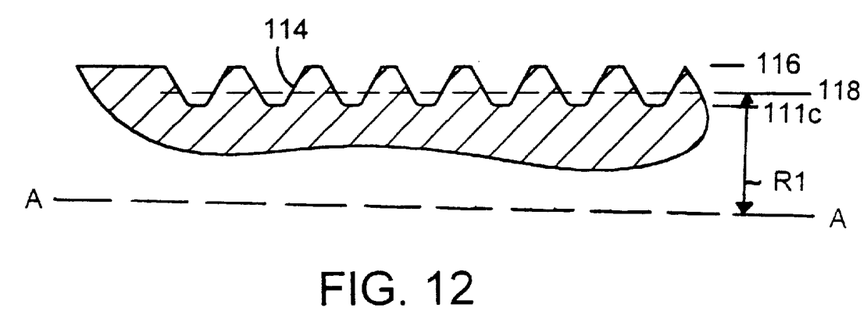
FIG. 12 is a longitudinal half-section taken along line 12—12 in FIG. 11.
Figure 13:
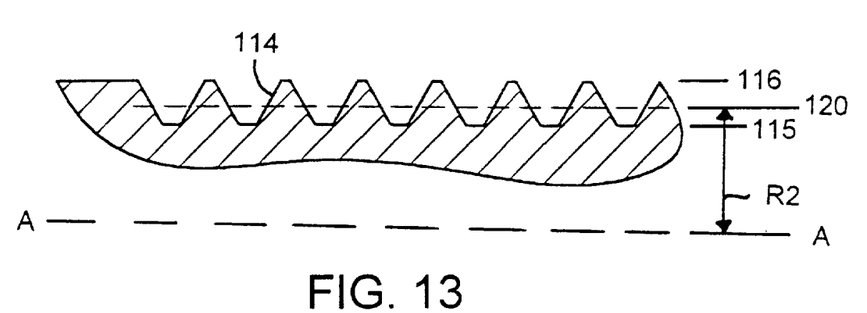
FIG. 13 is a longitudinal half-section taken along line 13—13 in FIG. 11.
Figure 14:
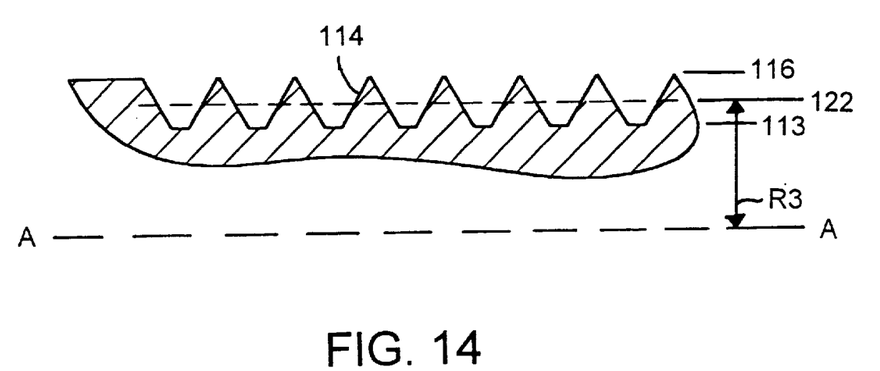
FIG. 14 is a longitudinal half-section taken along line 14—14 in FIG. 11.

FIGS. 12, 13, and 14 illustrate the cross-section through lines 12—12, 13—13, and 14—14, respectively, in FIG. 11. The troughs defined by dwell regions 113 in FIG. 14 are deeper than the troughs defined by the lobe 111c in FIG. 12. The troughs defined in the drop region 115 (FIG. 13) have depth that is between the depths of the troughs of the lobe 111c and the dwell regions 113. The peak diameters of the threads 114 along cylindrical locus 116 are the same in FIGS. 12, 13, and 14. Thus, although the threads 114 are cut deeper in the dwell region 113 illustrated in FIG. 14 than they are cut in the region of the lobe 111c illustrated in FIG. 12 or the drop region 115 in FIG. 13, the major diameter of the threads 114 does not change.

Figure 15:
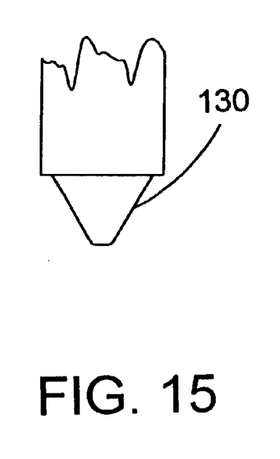
FIG. 15 represents a thread-forming tool useful to make the implant.

The threads 114 may be cut with a tool such as the tool 130 shown in FIG. 15, which has a shape that can be pushed into the main body 112 as it is turned in a lathe according to a cyclical pattern to form the alternating lobes 111, drop regions 115, and dwell regions 113. When this tool 130 is pushed into the main body 112 far enough to form a dwell region 113, the threads 114 are made thinner near their major diameter than when the tool 130 is pushed in a short distance to form lobes 111. As a result, the pitch diameters 118, 120, and 122 (and pitch radii) of the threads 114 shown in FIGS. 12, 13, and 14 become progressively smaller. Thus, pitch radius R1 (FIG. 12) is larger than pitch radius R2 (FIG. 13) which is larger than the pitch radius R3 (FIG. 14).

Figure 16:
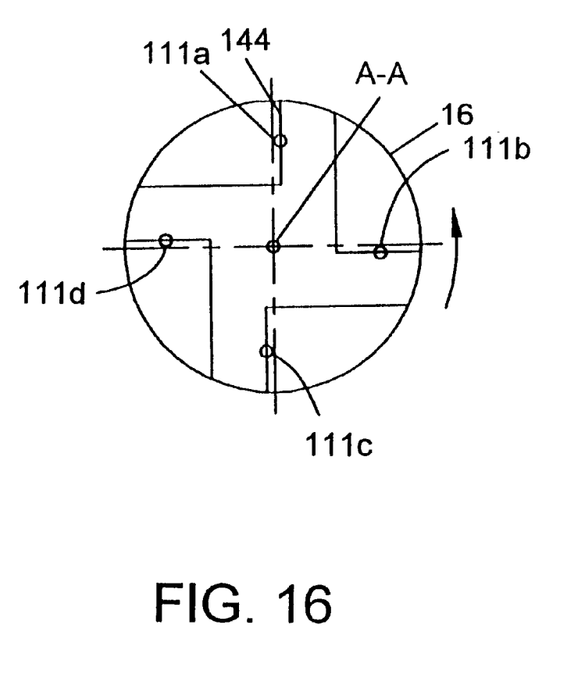
FIG. 16 schematically illustrates a property of the invention.

The illustrated dental implant 110' has a tapered end part 140 (FIG. 8) wherein both the peaks and the troughs of the threads taper on respective substantially conical loci toward the extreme end 142 (FIG. 8) of the main body 112'. This tapered end part 140 is fitted with four self-tapping cutting means arrayed symmetrically around the axis A—A, of which one 44 is shown in FIG. 16. As is apparent in FIG. 16 which illustrates schematically the relationship of the self-tapping cutting means and the lobes 111, each cutting means is aligned with one of the lobes 111 and, therefore, with the larger pitch diameter. However, the lobes 111 can be misaligned from the self-tapping cutting means.

Various alternatives exist from the embodiment shown in FIGS. 8–16. For example, the angles X, Y, and Z are shown having a summation that is substantially 90°. However, the summation of these angles, which dictates the angular position between adjacent lobes 111, could be greater than or less than 90°. Thus, when viewing the implant 110 from the side, the lobes 111 may spiral in the same direction as the spiraling of the threads 114, or in a direction that is opposite the spiraling of the threads 114. As the angle representing the summation of angles X, Y, and Z increases or decreases from 90°, the more profound the spiraling of the lobes 111 will be.

Also, the major diameter of the threads 114 can be recessed as well in the dwell region 113. This is accomplished by inserting the tool further toward the axis A—A of implant 110 shown in FIG. 14. Thus, the cylindrical locus 116 (FIG. 11) of the major diameter of the threads 114 would be altered to a non-cylindrical locus.

Figure 17:
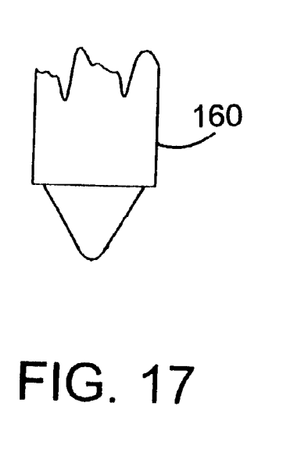
FIG. 17 is an alternative cutting tool for forming threads.

The tool used to develop the troughs between two vertically adjacent threads can also be rounded such as the rounded tool 160 in FIG. 17. Thus, in FIGS. 12–14, the area between two vertically adjacent threads would be defined by rounded sides of the threads instead of the flat sides of the threads 114 shown in FIGS. 12–14. By rounding these sides between vertically adjacent threads the total surface area to which the bone tissue attaches is increased. Furthermore, the tool can also have offset cutting regions which cause the lobe to be cut at a different circumferential position near one side of a thread than at the opposing side of the vertically adjacent thread which forms the trough.

Additionally, the lobes 111 may only be located on portions of the implant 110 or the amount of relief, defined by distance "D" in the dwell region 113, may be reduced. For example, when the implant 110 is used as a dental implant that is inserted into the jawbone, a portion of the implant 110 is located in the denser bone tissue of the cortical bone. Denser bone grows at a slower rate. Thus, because the bone tissue must grow toward the implant 110 for distance "D" in FIG. 11, it may be appropriate to decrease distance "D" in the region adjacent to the cortical bone to reduce the time required for complete osseointegration in that dense bone region. It may even be desirable to have no relief ("D"=0) in the region of the denser cortical bone. However, in the less dense cancellous bone beyond the cortical bone, distance "D" may be an acceptable distance across which the cancellous bone may grow.

Furthermore, the implant 110 incorporating this invention may have its surface treated by acid etching and/or grit blasting. A novel way in which these surfaces are treated is illustrated in Ser. No. 08/351,214, filed Nov. 30, 1994, which is herein incorporated by reference in its entirety.

We claim:

1. An implant for implantation into bone tissue having an exterior surface comprising:

an elongated body having a distal end portion for being submerged in said bone tissue, a proximal end portion for being located near said exterior surface of said bone tissue, a central axis, and an outer surface, said elongated body having a non-circular cross-section transverse to said central axis, said non-circular cross-section including a plurality of lobes and a plurality of dwells, each of said plurality of dwells being circumferentially disposed between adjacent ones of said plurality of lobes; and at least one thread making a plurality of turns around said elongated body and extending radially outward with respect to said central axis from said outer surface of said elongated body between said distal end portion and said proximal end portion.

2. The implant of claim 1 wherein said distal end portion of said elongated body includes a self-tapping screw-threaded region.

3. The implant of claim 2 wherein said self-tapping screw-threaded region includes multiple cutting surfaces, one of said plurality of lobes being axially aligned with one of said multiple cutting surfaces.

4. The implant of claim 2 wherein said at least one thread has a major diameter measured transverse said central axis, said major diameter being substantially constant between said proximal end portion and said self-tapping screw-threaded region.

5. The implant of claim 4 wherein said at least one thread has a crest defining said major diameter, said crest being flattened to present an axially extending surface in regions near said plurality of lobes and being an edge in regions near said plurality of dwells.

6. The implant of claim 2 wherein said plurality of lobes and said plurality of dwells decrease in their radial dimensions with respect to said central axis in said self-tapping screw-threaded region of said distal end portion.

7. The implant of claim 1 wherein said at least one thread has a major diameter measured transverse said central axis, said major diameter being substantially constant between said distal and proximal end portions.

8. The implant of claim 7 wherein said at least one thread has a crest defining said major diameter, said crest being flattened to present an axially extending surface in regions near said plurality of lobes and being an edge in regions near said plurality of dwells.

9. The implant of claim 7 wherein said at least one thread has a crest defining said major diameter, said crest being flattened to present an axially extending surface.

10. The implant of claim 1 wherein said at least one thread has a pitch radius measured from said central axis, said pitch radius being larger in regions near said plurality of lobes than in regions near said plurality of dwells.

11. The implant of claim 1 wherein said plurality of lobes and said plurality of dwells decrease in their radial dimensions with respect to said central axis at said distal end portion.

12. The implant of claim 1 wherein said outer surface of said elongated body is a root of said at least one thread, said root being a curved surface.

13. The implant of claim 1 wherein a central point of each of said plurality of dwells has a radius measured from said central axis, said radii having different values depending on the distance from said proximal end portion.

14. The implant of claim 13 wherein said radii of said plurality of dwells adjacent said proximal end portion are larger than said radii of said plurality of dwells on the remaining portions of said elongated body.

15. The implant of claim 14 wherein said radii of said plurality of dwells adjacent said proximal end portion are substantially the same as the radii of said plurality of lobes adjacent said proximal end portion.

16. The implant of claim 1 wherein at least one of said plurality of dwells has a central region that is substantially flat when viewed in said cross-section.

17. The implant of claim 1 wherein at least one of said plurality of dwells has a central region that is substantially curvilinear when viewed in said cross-section.

18. The implant of claim 17 wherein each of said plurality of dwells between said distal end portion and said proximal end portion are substantially curvilinear, said plurality of dwells being in a substantially cylindrical locus.

19. The implant of claim 18 wherein each of said plurality of lobes between said distal end portion and said proximal end portion project outwardly from said substantially cylindrical locus and have peaks, said peaks being on a second substantially cylindrical locus.

20. The implant of claim 19 wherein the number of each of said pluralities of lobes and dwells is four in said transverse direction, each of said four dwells and each of said four lobes extending an angular length of approximately 45° around said central axis.

21. The implant of claim 1 wherein said at least one thread has a variable major radius measured from said central axis in said cross-section, said major radius being larger in regions adjacent said lobes than in regions adjacent said dwells.

22. The implant of claim 1 wherein said adjacent ones of said plurality of lobes are circumferentially positioned from each other at a predetermined angle, said predetermined angle not being a multiple of 90° such that said plurality of lobes spiral along the axial length of said elongated body when viewed from the side.

23. The implant of claim 1 wherein the surfaces of said implant on said elongated body and said at least one thread undergo a treatment to enhance osseintegration.

24. The implant of claim 23 wherein said treatment includes grit-blasting.

25. The implant of claim 23 wherein said treatment includes acid-etching.

26. An implant for implantation into bone tissue having an exterior surface comprising:

an elongated body having a distal end portion for being submerged in said bone tissue, a proximal end portion for being located near said exterior surface of said bone tissue, a central axis, and an outer surface; and a plurality of threads extending radially outward from said outer surface of said elongated body between said distal end portion and said proximal end portion, said plurality of threads having a substantially constant major radius and varying minor radius, said varying minor radius defining a plurality of lobes and a plurality of dwells, each of said plurality of dwells having a generally flat region when viewed axially with respect to said central axis and being circumferentially disposed between adjacent ones of said plurality of lobes, each of said plurality of lobes being substantially curvilinear when viewed axially with respect to said central axis, said plurality of dwells and lobes giving said elongated body a non-circular cross-section when taken transversely to said central axis; and a self-tapping screw-threaded region within said distal end portion including a plurality of cutting surfaces, each of said cutting surfaces being substantially axially aligned with one of said lobes, each of said major and minor radii of said plurality of threads being smaller in said self-tapping screw-threaded region than in the remaining portions of said elongated body.

27. The implant of claim 26 wherein an average value of said minor radius through one rotation of said plurality of threads in regions outside of said self-tapping screw-threaded region have different values depending on the distance from said proximal end portion.

28. The implant of claim 27 wherein the average value of said minor diameter of said plurality of threads adjacent said proximal end portion is larger than the average value on the remaining portions of said elongated body.

29. The implant of claim 27 wherein the surfaces of said implant on said elongated body and said threads undergo a treatment to enhance osseintegration.

30. The implant of claim 29 wherein said treatment includes grit-blasting.

31. The implant of claim 29 wherein said treatment includes acid-etching.

32. An implant for implantation into bone tissue having an exterior surface comprising:

an elongated body having a distal end portion for being submerged in said bone tissue, a proximal end portion for being located near said exterior surface of said bone tissue, a central axis, and an outer surface; and a plurality of threads extending radially outward from said outer surface of said elongated body between said distal end portion and said proximal end portion, said plurality of threads having a substantially constant major radius and varying minor radius, said varying minor radius defining a plurality of lobes and a plurality of dwells, each of said plurality of dwells having a curvilinear region and being circumferentially disposed between adjacent ones of said plurality of lobes, each of said plurality of lobes being substantially curvilinear when viewed axially with respect to said central axis, said plurality of dwells and lobes giving said elongated body a non-circular cross-section when taken transversely to said central axis, each of said plurality of dwells between said proximal and distal end portions defining a generally cylindrical locus, each of said plurality of lobes projecting outwardly from said generally cylindrical locus; and a self-tapping screw-threaded region within said distal end portion including a plurality of cutting surfaces, each of said cutting surfaces being substantially axially aligned with one of said lobes, each of said major and minor radii of said plurality of threads being smaller in said self-tapping screw-threaded region than in the remaining portions of said elongated body.

33. The implant of claim 32 wherein an average value of said minor radius through one rotation of said plurality of threads in regions outside of said self-tapping screw-threaded region differs depending on the distance from said proximal end portion.

34. The implant of claim 32 wherein the average value of said minor diameter of said plurality of threads adjacent said proximal end portion is larger than the average value on the remaining portions of said elongated body.

35. The implant of claim 32 wherein the surfaces of said implant on said elongated body and said threads undergo a treatment to enhance osseintegration.

36. The implant of claim 35 wherein said treatment includes grit-blasting.

37. The implant of claim 35 wherein said treatment includes acid-etching.

38. A method of installing an implant into bone tissue though the exterior surface of said bone tissue, comprising the steps of:

preparing a bore in said bone tissue through said exterior surface of said bone tissue;

tapping said bore;

providing an implant having an elongated body and at least one thread for engaging the bone tissue defining said bore, said elongated body having a distal end portion to be submerged in said bone tissue, a proximal end portion for being located near said exterior surface of said bone tissue, a central axis, and an outer surface, said elongated body having an non-circular shaped cross-section;

inserting said distal end of said implant into said bore; and screwing said implant into said bore so that when viewed in cross-section only portions of said elongated body contact said bone tissue defining said bore so as to reduce the friction between said bone tissue and said implant.

39. The method of claim 38, wherein said implant includes a self-tapping screw-threaded region within said distal end portion including a plurality of cutting surfaces, said steps of tapping said bore and screwing said implant into said bore are accomplished simultaneously.

40. The method of claim 38, wherein said at least one thread has a varying minor radius defining a plurality of lobes and a plurality of dwells, each of said plurality of dwells being disposed between adjacent ones of said plurality of lobes, said plurality of lobes being said bone-contacting portions of said implant.

41. The method of claim 38, wherein said at least one thread has a crest defining a non-constant major radius, only portions of said crest contacting said bone tissue.

42. A method of securing an implant in bone tissue, said implant being installed though the exterior surface of said bone tissue, comprising the steps of:

preparing a bore in said bone tissue through said exterior surface of said bone tissue;

tapping said bore;

providing an implant having an elongated body and at least one thread for engaging the bone tissue defining said bore, said at least one thread making a plurality of turns around said elongated body, said elongated body having a distal end portion to be submerged in said bone tissue, a proximal end portion for being located near said exterior surface of said bone tissue, a central axis, and an outer surface, said elongated body having regions for receiving said bone tissue residing entirely between adjacent turns of said at least one thread, said regions extending inwardly toward said central axis thereby giving said elongated body a non-circular cross-section;

installing said implant into said bore; and allowing said bone tissue to grow into said regions between adjacent turns of said at least one thread.

43. The method of claim 42 wherein the surfaces of said implant on said elongated body and said threads undergo a treatment to enhance osseintegration.

44. The method of claim 43 wherein said treatment includes grit-blasting.

45. The method of claim 43 wherein said treatment includes acid-etching.

* * * * *